United States Patent [19]
Oshika et al.

[11] Patent Number: 5,747,015
[45] Date of Patent: May 5, 1998

[54] ACYLATED SILK PROTEINS FOR HAIR CARE

[75] Inventors: Masato Oshika; Sachio Naito, both of Tochigi, Japan

[73] Assignee: Kao Corporation, Tokyo, Japan

[21] Appl. No.: 636,264

[22] Filed: Apr. 24, 1996

[30] Foreign Application Priority Data

May 19, 1995 [JP] Japan .................................. 7-121182

[51] Int. Cl.$^6$ .................................. A61K 7/00; A61K 7/06
[52] U.S. Cl. .................. 424/70.14; 424/70.1; 424/70.11; 510/119
[58] Field of Search ................................ 424/70.1, 70.11, 424/70.14, DIG. 2; 514/773; 510/119, 121

[56] References Cited

U.S. PATENT DOCUMENTS 5,476,649  12/1995  Naito et al. ............................ 424/70.1

FOREIGN PATENT DOCUMENTS 6-122610   5/1994   Japan .

*Primary Examiner*—Robert H. Harrison
*Attorney, Agent, or Firm*—Oblon, Spivak, McClelland, Maier & Neustadt, P.C.

[57] ABSTRACT

A hair care product which comprises a salt of an acylated compound obtained by condensing fatty acids containing at least 40% of branched fatty acids having 20 to 32 carbon atoms with silk protein-derived peptides, which hair care product is effective in imparting a good texture and preventing the hair from damages (split hair, clipped hair, etc.) without giving any tackiness or greasiness.

2 Claims, No Drawings

ACYLATED SILK PROTEINS FOR HAIR CARE

FIELD OF THE INVENTION

This invention relates to a hair care product which is excellent in the effects of preventing hair damages and imparting a good texture to the hair.

BACKGROUND OF THE INVENTION

With the recent tendency toward diversified fashion, long-haired styles have been firmly established. Moreover, variations on these long-haired styles become popular owing to hairdressing treatments such as partial permanent waving. Under these circumstances, there arises a serious problem of increasing hair damages (split hair, clipped hair, etc.). The cause of these hair damages seemingly resides in that the keratin protein is denatured by chemical treatments (permanent waving, etc.) and the hair thus weakened is liable to be affected by physical treatments (drying with a dryer, brushing, etc.).

As countermeasures against the deterioration of the protein structure due to chemical treatments, from the above-mentioned hair damages, attempts have been made to form a protective film on the surface of the hair and improve the heat-retention and elasticity of the hair by using various hair care products containing collagen, keratin protein, etc. Furthermore, attempts have been made to relieve the friction on the surface of the hair by adding oily components such as higher alcohols, esters, liquid paraffin, silicone oil, etc. to hair rinses, hair treatments and brushing aids.

Although collagen, keratin protein and hydrolysates thereof can exert effects of preventing hair damages due to chemical treatments (permanent waving, etc.) to a certain extent, these effects are still unsatisfactory. Because of being effective in reducing friction on the surface of the hair, etc., the above-mentioned oily components exerts preventive effects on hair damages to a certain extent and thus impart a temporary good feel in using. However, they fail to exert any lasting effect on the damaged hair. That is to say, no satisfactory treatment effect can be achieved thereby. When these oily components are used in a large amount in hair care products, moreover, there arises another problem that the enhanced tackiness and greasiness worsen the feel of the prdouct in using.

Accordingly, it has been required to develop a hair care product which is free from any tackiness or greasiness, shows good conditioning effects (moist feel in using, etc.), exerts excellent effects on the damaged hair and is efficacious in repairing the inherent functions of the hair and sustaining the same.

Under these circumstances, the present inventors have conducted extensive studies. As a result, they have found out that when a hair care product comprising a condensation product of branched fatty acids having 20 to 32 carbon atoms with silk protein-derived peptides is applied to chemically treated (permed, etc.) hair, the hair care product surprisingly exerts excellent conditioning effects (i.e., imparting a moist feel, softness, smoothness, gloss, etc.) even on dry hair and these effects are not lost even after shampooing the hair repeatedly. The present invention has been completed based on this finding.

SUMMARY OF THE INVENTION

Accordingly, an object of the present invention is to provide a hair care product which comprises a salt of an acylated compound obtained by condensing fatty acids containing at least 40% of branched fatty acids having 20 to 32 carbon atoms with silk protein-derived peptides.

DETAILED DESCRIPTION OF THE INVENTION

The fatty acids to be used in the present invention are branched fatty acids having 20 to 32 carbon atoms. Branched fatty acids having less than 20 carbon atoms are insufficient in the adsorption onto the hair and, therefore, fail to achieve a satisfactory effect of repairing hair damages. On the other hand, it is not preferable to use branched fatty acids having 33 or more carbon atoms from the viewpoints of solubility and tackiness after the treatment. Moreover, linear fatty acids having less than 20 carbon atoms are not preferable from the viewpoints of solubility, texture and effects. Thus it is preferable, from the viewpoints of texture and effects, to use a condensation product of fatty acids containing at least 40% of branched fatty acids.

The branched fatty acids to be used in the present invention may be either natural ones or synthetic ones. Examples of a single fatty acid include branched fatty acids such as eicosanoic acid, heneicosanoic acid, behenic acid, lignoceric acid, cerotic acid, montanic acid and melissic acid. These fatty acids can be separated or extracted from the hair, etc. in accordance with, for example, a method described in "LIPIDS, Vol. 23, No. 9, p 878–881 (1988)". Alternatively, they may be synthesized in accordance with a methods described in Columns (3) to (5) in JP-A-4-139734 (The term "JP-A" as used herein means an "unexamined published Japanese patent application").

In addition to such a single fatty acid residue as described above, it is also possible to use, as the branched fatty acids in the present invention, fatty acids obtained by removing fatty acid residues having less than 20 carbon atoms and those having 36 or more carbon atoms from natural mixed fatty acid residues (lanolin fatty acid residues, etc.) by, for example, fractional distillation. A large amount of anti-iso branched fatty acids are contained not only in lanolin fatty acids separated and purified from lanolin but also in hard lanolin fatty acids and soft lanolin fatty acids purified from the lanolin fatty acids. Thus it is also possible to use these fatty acids therefor. More particularly speaking, lanolin fatty acids contain about 29% of anti-iso branched fatty acids together with about 25% of α-hydroxy linear fatty acids, about 22% of iso branched fatty acids, about 7% of linear fatty acids, about 3% of α-hydroxyiso branched fatty acids and about 14% of unidentified components.

In order to fully achieve the effects of the present invention, it is preferable to use lanolin fatty acids containing at least 20% of anti-iso branched fatty acids, still preferably anti-iso branched fatty acids having 20 to 32 carbon atoms.

As the silk protein-derived peptides, i.e., another fundamental component of the branched fatty acid/silk protein-derived peptide condensation product, it is preferable to use silk protein hydrolysates, for example, those having an average molecular weight of 200 to 5,000, still preferably 300 to 600. Silk protein hydrolysates having an average molecular weight of less than 200 show only a poor effect of repairing the damaged hair. When the average molecular weight thereof exceeds 5,000, the effects based on the alkyl groups in the branched fatty acid/silk protein-derived peptide condensation product are seriously declined and thus the adsorption onto the hair and the texture are worsened.

These silk protein-derived peptides can be obtained by, for example, hydrolyzing silk protein with the use of acids, alkalis or enzymes (JP-B-59-29199, etc., the term "JP-B" as used herein means an "examined Japanese patent publication").

The branched fatty acids and the silk protein-derived peptides are condensed in the following manner. Namely, the silk protein-derived peptides are acylated by a conventional method (i.e., Schotten-Baumann reaction) by using acid chlorides of the branched fatty acids in an aqueous solution (pH 7–14, preferably pH 8–9.5) to thereby give an aqueous solution containing not more than 60% by weight, preferably from 30 to 40% by weight, of the branched fatty acid/silk protein-derived peptide condensation product as solid components. The aqueous solution thus obtained may be used in the hair care product of the present invention as such. Alternatively, it may be dried and then employed in the form of a powder, etc.

It is also possible to synthesize the branched fatty acid/silk protein-derived peptide condensation product by a well-known method wherein methyl esters of branched fatty acids are condensed with silk protein-derived peptides, or another method [Column (5), JP-A-4-30851] wherein protein-derived peptides are esterified. Esterification is performed by treating the silk protein-derived peptides with a reducing agent to thereby form thiol groups, removing the moisture by concentration under reduced pressure, freeze-drying, spray drying, etc., mixing the residue with branched fatty acids in a water-free organic solvent similar to the case of esterification of fats or oils, heating and then stirring for a definite period of time in the presence of an acid or alkali catalyst (preferably an acid catalyst).

As the esterification proceeds, the silk protein-derived peptides are gradually dissolved in the reaction mixture. Thus the progress of the esterification can be monitored by observing the dissolution. After the completion of the reaction, an alkali (when an acid catalyst is used in the reaction) or an acid (when an alkali catalyst is used therein) is added to thereby neutralize the reaction mixture. Then the salt thus precipitated is filtered off. The branched fatty acid/silk protein-derived peptide condensation product thus obtained may be used in the form of a solution usually in a lower alcohol such as ethanol. Alternatively, it may be dried and then employed in the form of a powder, etc.

In addition to the methods as described above, it is also possible to obtain the branched fatty acid/silk protein-derived peptide condensation product through the acylation of thiol groups in cysteine residues in the silk protein-derived peptides.

It is also possible to synthesize the branched fatty acid/silk protein-derived peptide condensation product by reacting anhydrous branched fatty acids or branched fatty acid chlorides with thiol group in the presence of trifluoroacetic acid (JP-B-5-508405).

The solution of the branched fatty acid/silk protein-derived peptide condensation product thus obtained is cooled to room temperature. Next, various preservatives and various additives may be added thereto so as to improve its odor and transparency. Further, it is preferable to decolor the branched fatty acid/silk protein-derived peptide condensation product with active carbon or to regulate its concentration by distilling off the excessive lower alcohol or filtration.

The content of this branched fatty acid/silk protein-derived peptide condensation product in the hair care product of the present invention preferably ranges from 0.01 to 20% (by weight, the same will apply hereinafter), still preferably from 0.1 to 10%. When its content is less than 0.01%, the effects of the present invention cannot be fully achieved. When it exceeds 20%, the texture is sometimes worsened (becoming tacky, etc.).

The hair care product of the present invention may contain surfactants. Particular examples thereof include anionic surfactants such as alkylbenzenesulfonates, alkyl ether sulfates, olefinsulfonates, α-sulfo fatty acid esters, amino acid-based surfactants, phosphate-based surfactants and sulfosuccinate-based surfactants; amphoteric surfactants such as sulfonic acid type surfactants, betaine type surfactants, alkylamine oxides and imidazoline type surfactants; nonionic surfactants such as polyoxyethylene alkyl ethers, polyoxyethylene alkylphenyl ethers, alkanolamides and alkylene oxide adducts thereof, esters of polyhydric alcohols with fatty acids, sorbitan fatty acid esters and alkylsaccharide-based surfactants; and cationic surfactants such as mono- or di-linear long chain alkyl quaternary ammonium salts and mono- or di-branched long chain alkyl quaternary ammonium salts. Either one of these surfactants or a combination thereof may be selected depending on the performances of various hair care products. When the hair care product of the present invention is in the form of a shampoo, in particular, it is preferable to use amino acid-based surfactants, phosphate-based surfactants, sulfosuccinate-based surfactants, imidazoline type surfactants, alkylsaccharide-based surfactants, etc. from the viewpoint of irritation to the skin and hair.

The content of these surfactants in the hair care product of the present invention preferably ranges from 0.01 to 40%, still preferably from 0.05 to 20%.

To improve the texture of the hair and skin, the hair care product of the present invention may further contain one or more cationic polymers selected from cationized cellulose derivatives, cationized starch, cationized guar gum derivatives, diallyl quaternary ammonium salts/acrylamide copolymers, quaternized polyvinylpyrrolidone derivatives, polyglycolamine condensation products, etc.

Particularly preferable examples of these cationic polymers include cationized cellulose having a molecular weight of about 100,000 to 3,000,000, cationized guar gum having a degree of cationization of about 0.01 to 1 (for example, "Jaguar" manufactured by MEIHOLE CO., LTD.), diallyl quaternary ammonium salt/acrylamide copolymers having a molecular weight of about 30,000 to 2,000,000, quaternized polyvinylpyrrolidone derivatives such as a quaternized product of polyvinylpyrrolidone/dimethylaminoethyl methacrylate having a molecular weight of about 10,000 to 2,000,000 and containing from 1.8 to 2.4% of cationic nitrogen in the vinyl polymer, polyglycol polyamine condensation products having an alkyl group having 6 to 10 carbon atoms, adipic acid/dimethylaminohydroxypropyl diethylenetriamine copolymer ("CARTERETIN", manufactured by Sandoz, Inc., etc.) and cationic polymers described in JP-A-53-139734 and JP-A-60-36407.

The content of the cationic polymer in the hair care product of the present invention preferably ranges from 0.05 to 20%, still preferably from 0.1 to 10%.

To further improve the texture of the hair or the skin, the hair care product of the present invention may contain one or more silicone derivatives such as dimethyl polysiloxane, methylphenyl polysiloxane, amino-modified silicone, alcohol-modified silicone, aliphatic alcohol-modified silicone, polyether-modified silicone, epoxy-modified silicone, fluorine-modified silicone, cyclic silicone or alkyl-modified silicone. Such a silicone derivative may be used as a single material. Alternatively, use can be made of a latex composition prepared by emulsion polymerization in accordance with, for example, the method described in JP-A-56-38609.

It is particularly preferable to use dimethyl polysiloxane (degree of polymerization: 500 or above), polyether-modified silicone, amino-modified silicone, cyclic silicone, etc., from these silicone derivatives, since they are capable of imparting a good texture to the hair.

The content of the silicone derivative in the hair care product of the present invention preferably ranges from 0.01 to 20%, still preferably from 0.05 to 10%.

The hair care product of the present invention can further contain various components commonly employed in hair care products, for example, texture improvig agents (e.g., higher fatty acid salts, alkylamine oxides, fatty acid alkanolamides, squalene, lanolin, α-monoisostearyl glyceryl ether, cholesteryl sulfate, etc.); moisturelizer [e.g., propylene glycol, glycerol, sorbitol, amide derivatives described in JP-A-64-9913 and represented by the following formula (1):

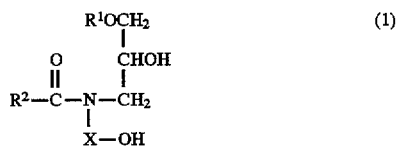

wherein $R^1$ represents a linear or branched, saturated or unsaturated hydrocarbon group having 10 to 26 carbon atoms; $R^2$ represents a linear or branched, saturated or unsaturated hydrocarbon group having 9 to 25 carbon atoms; and X represents —$(CH_2)_n$— wherein n is an integer of from 2 to 6; dialkylene glycol monoalkyl ethers represented by the following formula (2):

wherein $R^3$ represents a hydrogen atom or a methyl group; and $R^4$ represents an alkyl group having 1 to 5 carbon atoms; etc.]; viscosity regulating agents (methyl cellulose, carboxyvinyl polymer, hydroxyethyl cellulose, polyoxyethylene glycol distearate, ethanol, etc.); bactericides (trichloric acid, trichlorocarban, etc.); anti-inflammatory agents (potassium glycyrrhetiniate, tocopherol acetate, etc.); anti-dandruff agents (zinc pyrithione, octopirox, etc.); preservatives (methylparaben, butylparaben, etc.); pearling agents, perfumes, colorants, UV absorbers, antioxidants, etc., so long as the effects of the present invention are not deteriorated thereby.

It is preferable that the pH value of the hair care product of the present invention is regulated to pH 3 to 10, still preferably pH 4 to 8, with the use of well-known acidic or alkaline chemicals which have been commonly employed in hair care products.

The term "hair care product" as used herein involves all toiletry products to be applied to the hair. Examples thereof include pre-shampoo products, shampoo products, hair rinses, hair conditioners, hair treatments, setting lotions, blow-styling lotions, hair sprays, hair-styling foams, hair-styling gels, hair liquids, hair tonics, hair creams, permanent waving agents of type I, permanent waving agents of type II, permanent hair dyes, temporary hair dyes, etc.

Further, the hair care product of the present invention may be processed into various forms (aqueous solution, ethanolic solution, emulsion, suspension, gel, liquid crystal, solid, aerosol, etc.) depending on the purpose of the use.

The hair care product of the present invention imparts a good texture to the hair without giving any tackiness or greasiness. Moreover, it is efficacious in preventing hair damages such as split or clipped hair.

To further illustrate the present invention in greater detail, and not by way of limitation, the following Examples will be given.

SYNTHESIS EXAMPLE 1

Synthesis of lanolin fatty acid/silk protein-derived peptide condensation product:

600 g of a 30% aqueous solution of silk protein-derived peptides (average molecular weight: 1,000) was adjusted to pH 9.5 with an aqueous solution of sodium hydroxide. Next, 66 g of lanolin fatty acid chloride was added to the aqueous solution of silk protein-derived peptides. After the completion of the addition, the solution was heated to 60° C. and maintained at this temperature for 120 minutes. Then this solution was adjusted to pH 6.5 with hydrochloric acid and the content of dry solid components therein was adjusted to 35% with distilled water.

SYNTHESIS EXAMPLE 2

Synthesis of 18-methyleicosanoic acid/silk protein-derived peptide condensation product:

600 g of a 30% aqueous solution of silk protein-derived peptide (average molecular weight: 500) was adjusted to pH 9.0 with an aqueous solution of sodium hydroxide. Next, 36 g of 18-methyleicosanoic acid chloride was added to the aqueous solution of silk protein-derived peptides. After the completion of the addition, the solution was heated to 60° C. and maintained at this temperature for 120 minutes. Then this solution was adjusted to pH 6.8 with hydrochloric acid and the content of dry solid components therein was adjusted to 25% with distilled water.

EXAMPLES 1 TO 5 AND COMPARATIVE EXAMPLES 1 TO 6

Shampoo compositions as shown in Table 1 were prepared and evaluated in performance. The results are shown in Table 1.

Evaluation method:

(1) Warm water (about 40° C.) was absorbed into a hair bundle (length: about 15 to 20 cm, weight: about 20 g) of a Japanese woman who had cold-permed the hair thrice. Then 1 g of a shampoo composition was applied uniformly to the hair bundle and foamed for 1 minute. After rinsing with running water and drying, the hair was evaluated in softness, moist feel, gloss and smoothness in accordance with the following criteria.

(Softness)
 ⊚: very soft.
 O: soft.
 Δ: moderate.
 x: stiff.
(Greasiness)
 ⊚: very little.
 O: little.
 Δ: moderates
 x: greasy.
(Gloss and smoothness)
 ⊚: very good.

O: good.

Δ: moderate.

x: poor.

(2) A hair bundle was treated in the same manner as the one described in the above (1). After brushing a definite times, the occurrence of split hair was evaluated in comparison with the unbrushed hair in accordance with the following criteria.

⊙: no increase in split hair.

O: little increase in split hair.

Δ: somewhat increase in split hair.

x: serious increase in split hair.

Evaluation method:

A hair bundle (length: about 15 to 20 cm, weight: about 20 g) of a Japanese woman who had cold-permed the hair thrice was washed with a common shampoo product. Then 2 g of a hair treatment composition was applied uniformly to the hair bundle. After rinsing with running water for 30 minutes and drying with towel, the hair in a moisten state was evaluated in accordance with the same criteria as in Example 1. Further, the hair was dried with a dryer and the hair in a dry state was evaluated in accordance with the same criteria as in Example 1.

TABLE 1

| Component (%) | Example | | | | | Comparative Example | | | | | |
|---|---|---|---|---|---|---|---|---|---|---|---|
| | 1 | 2 | 3 | 4 | 5 | 1 | 2 | 3 | 4 | 5 | 6 |
| Polyoxyethylene(3) lauryl ether sodium | 15 | 15 | 15 | — | — | 15 | — | 15 | 15 | 15 | 15 |
| N-lauroyl-N-carboxymethyl-N-(hydroxy-ethyl)ethylenediamine triethanolamine salt | — | — | — | 15 | 15 | — | 15 | — | — | — | — |
| Silk protein-derived polypeptide/branched behenic acid condensation product sodium salt | 3 | — | — | 3 | — | — | — | — | — | — | — |
| Silk protein-derived polypeptide/branched montanic acid condensation product sodium salt | — | 3 | — | — | — | — | — | — | — | — | — |
| Silk protein-derived polypeptide/lanolic acid long chain fraction condensation product sodium salt | — | — | 3 | — | 3 | — | — | — | — | — | — |
| Silk protein-derived polypeptide/myristic acid condensation product sodium salt | — | — | — | — | — | — | — | — | 3 | — | — |
| Silk protein-derived polypeptide/stearic acid condensation product sodium salt | — | — | — | — | — | — | — | — | — | 3 | — |
| Collagen-derived polypeptide/behenic acid condensation product sodium salt | — | — | — | — | — | — | — | — | — | — | 3 |
| Cation cellulose (Polymer JR400, by UCC) | — | — | — | — | — | 3 | — | — | — | — | — |
| Dimethyl polysiloxane (1000 cst) | — | — | — | — | — | — | 3 | — | — | — | — |
| Distearylammonium chloride | — | — | — | — | — | — | — | 3 | — | — | — |
| Water | the balance | ← | ← | ← | ← | ← | ← | ← | ← | ← | ← |
| (1) Softness | O | ⊙ | ⊙ | O | ⊙ | x | Δ | Δ | Δ | Δ | x |
| (2) Greasiness | O | ⊙ | ⊙ | O | ⊙ | x | x | x | Δ | Δ | Δ |
| (3) Gloss | O | ⊙ | ⊙ | O | ⊙ | Δ | Δ | Δ | x | O | Δ |
| (4) Smoothness | O | ⊙ | ⊙ | O | ⊙ | x | Δ | x | x | Δ | x |
| (5) Occurrence of split hair | O | ⊙ | ⊙ | O | ⊙ | x | Δ | x | x | Δ | x |

EXAMPLES 6 TO 10 AND COMPARATIVE EXAMPLES 7 TO 12

Hair treatment compositions as shown in Table 2 were prepared and evaluated in performance. The results are shown in Table 2.

TABLE 2

| Component (%) | Example | | | | | Comparative Example | | | | | |
|---|---|---|---|---|---|---|---|---|---|---|---|
| | 6 | 7 | 8 | 9 | 10 | 7 | 8 | 9 | 10 | 11 | 12 |
| Stearyltrimethylammonium chloride | 2 | — | 2 | 2 | — | 2 | — | 2 | 2 | 2 | 2 |
| N-(2-dodecyl)hexadecyl-N,N,N-trimethyl-ammonium chloride | — | 2 | — | — | 2 | — | 2 | — | — | — | — |
| Silk protein-derived polypeptide/branched behenic acid condensation product sodium salt | 3 | — | — | 3 | — | — | — | — | — | — | — |
| Silk protein-derived polypeptide/branched montanic acid condensation product sodium salt | — | 3 | — | — | — | — | — | — | — | — | — |
| Silk protein-derived polypeptide/lanolic acid long chain fraction condensation product sodium salt | — | — | 3 | — | 3 | — | — | — | — | — | — |

TABLE 2-continued

|  | Example | | | | | Comparative Example | | | | | |
| --- | --- | --- | --- | --- | --- | --- | --- | --- | --- | --- | --- |
| Component (%) | 6 | 7 | 8 | 9 | 10 | 7 | 8 | 9 | 10 | 11 | 12 |
| Silk protein-derived polypeptide/myristic acid condensation product sodium salt | — | — | — | — | — | — | — | — | 3 | — | — |
| Silk protein-derived polypeptide/stearic acid condensation product sodium salt | — | — | — | — | — | — | — | — | — | 3 | — |
| Collagen-derived polypeptide/behenic acid condensation product sodium salt | — | — | — | — | — | — | — | — | — | — | 3 |
| Cetyl alcohol | — | — | — | 15 | 15 | — | — | 15 | — | — | — |
| Hydroxy cellulose | 0.5 | 0.5 | 0.5 | 0.5 | 0.5 | 0.5 | 0.5 | 0.5 | 0.5 | 0.5 | 0.5 |
| Water | the balance | ← | ← | ← | ← | ← | ← | ← | ← | ← | ← |
| (1) Softness | ○ | ⊚ | ⊚ | ○ | ⊚ | Δ | Δ | Δ | Δ | Δ | x |
| (2) Greasiness | ○ | ⊚ | ⊚ | ○ | ⊚ | x | x | x | Δ | Δ | Δ |
| (3) Gloss | ○ | ⊚ | ⊚ | ○ | ⊚ | Δ | Δ | Δ | x | ○ | Δ |
| (4) Smoothness | ○ | ⊚ | ⊚ | ○ | ⊚ | Δ | Δ | Δ | x | Δ | x |
| (5) Occurrence of split hair | ○ | ⊚ | ⊚ | ○ | ⊚ | x | Δ | Δ | x | Δ | x |

Hair care products as shown in the following Examples 3 to 7 were prepared by conventional methods.

EXAMPLE 13

Hair treatment composition:

| (Component) | (% by weight) |
| --- | --- |
| (1) silk protein-hydrolysate/behenic acid condensation product sodium salt | 2.0 |
| (2) stearyltrimethylammonium chloride | 1.0 |
| (3) dimethyl polysiloxane | 1.5 |
| (4) cetostearyl alcohol | 3.0 |
| (5) isostearyl pentaerythritol glycidyl ether 1 mol adduct | 3.0 |
| (6) liquid paraffin | 3.0 |
| (7) hydroxyethyl cellulose | 0.5 |
| (8) polyoxyethylene oleyl ether (EO = 5) | 0.5 |
| (9) methylparaben | 0.2 |
| (10) perfume | 0.4 |
| (11) water | balance |

EXAMPLE 14

Conditioning foam composition:

| (Component) | (% by weight) |
| --- | --- |
| (1) silk protein-hydrolysate/lanolin fatty acid (long chain fraction) condensation product triethanolamine salt | 1.0 |
| (2) methylphenyl polysiloxane | 1.0 |
| (3) isotridecyl myristate | 1.0 |
| (4) 3-methyl-1,3-butanediol | 1.0 |
| (5) liquid paraffin | 2.5 |
| (6) 95% ethanol | 5.0 |
| (7) methylparaben | 0.1 |
| (8) perfume | 0.1 |
| (9) water | balance |

EXAMPLE 15

Hair cream composition:

| (Component) | (% by weight) |
| --- | --- |
| (1) silk protein-hydrolysate/behenic acid condensation product potassium salt | 2.0 |

-continued

| (Component) | (% by weight) |
| --- | --- |
| (2) cetyltrimethylammonium chloride | 1.0 |
| (3) cetyl alcohol | 5.0 |
| (4) amino-modified silicone | 2.0 |
| (5) liquid paraffin | 3.0 |
| (6) perfume | 0.1 |
| (7) water | balance |

EXAMPLE 16

Hair treatment composition:

| (Component) | (% by weight) |
| --- | --- |
| (1) silk protein-hydrolysate/anti-iso $C_{21}$ branched fatty acid condensation product sodium salt | 2.0 |
| (2) stearyltrimethylammonium chloride | 1.0 |
| (3) dimethyl polysiloxane | 1.5 |
| (4) cetostearyl alcohol | 3.0 |
| (5) liquid paraffin | 3.0 |
| (6) hydroxyethyl cellulose | 0.5 |
| (7) polyoxyethylene oleyl ether (EO = 5) | 0.5 |
| (8) methylparaben | 0.2 |
| (9) perfume | 0.4 |
| (10) water | balance |

While the invention has been described in detail and with reference to specific embodiments thereof, it will be apparent to one skilled in the art that various changes and modifications can be made therein without departing from the spirit and scope thereof.

What is claimed is:

1. A hair care product which comprises a salt of an acylated compound obtained by condensing fatty acids containing at least 40% of branched fatty acids having 22 to 32 carbon atoms with silk protein-derived peptides.

2. A hair care product as claimed in claim 1, wherein said fatty acids are lanolin fatty acids containing at least 20% by weight, in branched fatty acids, of anti-iso branched fatty acids.

* * * * *